(12) United States Patent
Zhang et al.

(10) Patent No.: US 11,768,163 B2
(45) Date of Patent: Sep. 26, 2023

(54) CT SYSTEM AND DETECTION DEVICE FOR CT SYSTEM

(71) Applicants: Nuctech Company Limited, Beijing (CN); Tsinghua University, Beijing (CN)

(72) Inventors: Li Zhang, Beijing (CN); Zhiqiang Chen, Beijing (CN); Qingping Huang, Beijing (CN); Yunda Sun, Beijing (CN); Xin Jin, Beijing (CN); Le Shen, Beijing (CN); Liang Li, Beijing (CN); Tiao Zhao, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 268 days.

(21) Appl. No.: 17/309,684

(22) PCT Filed: Sep. 10, 2019

(86) PCT No.: PCT/CN2019/105147
§ 371 (c)(1),
(2) Date: Jun. 15, 2021

(87) PCT Pub. No.: WO2020/125080
PCT Pub. Date: Jun. 25, 2020

(65) Prior Publication Data
US 2022/0042929 A1    Feb. 10, 2022

(30) Foreign Application Priority Data
Dec. 17, 2018   (CN) .......................... 201811542627.4

(51) Int. Cl.
*G01N 23/046* (2018.01)
*G01V 5/00* (2006.01)

(52) U.S. Cl.
CPC .......... *G01N 23/046* (2013.01); *G01V 5/005* (2013.01); *G01N 2223/639* (2013.01)

(58) Field of Classification Search
CPC .......... G01N 23/046; G01N 2223/639; G01N 2223/419; G01N 2223/423; G01V 5/005;
(Continued)

(56) References Cited

U.S. PATENT DOCUMENTS 9,572,540 B2 * 2/2017 Zhang .................. A61B 6/4241
10,339,673 B2   7/2019 Li et al.
(Continued)

FOREIGN PATENT DOCUMENTS

CN    202948145 U    5/2013
CN    204479498 U    7/2015
(Continued)

OTHER PUBLICATIONS

"International Application No. PCT/CN2019/105147, International Search Report and Written Opinion dated Nov. 28, 2019", (Nov. 28, 2019), 11 pgs.
(Continued)

*Primary Examiner* — Courtney D Thomas
(74) *Attorney, Agent, or Firm* — Schwegman Lundberg & Woessner, P.A.

(57) ABSTRACT

The present application discloses a CT system and a detection apparatus for the CT system. The detection apparatus includes: a high-energy detector assembly including a plurality of rows of high-energy detectors arranged along a predetermined trajectory; a low-energy detector assembly including a plurality of rows of low-energy detectors arranged at intervals along the predetermined trajectory, the low-energy detector assembly and the high-energy detector assembly being disposed in a stack; a number of rows of the low-energy detectors is smaller than a number or rows of the
(Continued)

high-energy detectors; and each row of the low-energy detectors covers a row of high-energy detectors.

12 Claims, 3 Drawing Sheets

(58) Field of Classification Search
CPC ...... G01V 5/0041; A61B 6/035; A61B 6/032; A61B 6/4233; A61B 6/4241; A61B 6/4266; G01T 1/2985
See application file for complete search history.

(56) References Cited

U.S. PATENT DOCUMENTS

| | | | |
|---|---|---|---|
| 2013/0058452 A1* | 3/2013 | Levene | G01T 1/2985 257/E27.129 |
| 2014/0037045 A1 | 2/2014 | Dafni et al. | |
| 2014/0110592 A1 | 4/2014 | Nelson et al. | |
| 2017/0309043 A1 | 10/2017 | Li et al. | |

FOREIGN PATENT DOCUMENTS

| | | |
|---|---|---|
| CN | 105054954 A | 11/2015 |
| CN | 204882412 U | 12/2015 |
| CN | 105758873 A | 7/2016 |
| CN | 105806856 A | 7/2016 |
| CN | 109471185 A | 3/2019 |
| EP | 2749873 A1 | 7/2014 |
| JP | 2015532974 A | 11/2015 |
| JP | 2016029367 A | 3/2016 |
| JP | 2016070752 A | 5/2016 |
| JP | 2018529083 A | 10/2018 |
| WO | WO-2020125080 A1 | 6/2020 |

OTHER PUBLICATIONS

"European Application No. 19897922.1, Extended European Search Report dated Aug. 1, 2022", (Aug. 1, 2022), 16 pgs.

"Japanese Application No. 2021-518535, Japanese Office Action dated May 9, 2022", (May 9, 2022), 8 pgs.

* cited by examiner

CT SYSTEM AND DETECTION DEVICE FOR CT SYSTEM

CROSS REFERENCE TO RELATED APPLICATION

This application is a U.S. national stage filing under 35 U.S.C. § 371 from International Application No. PCT/CN2019/105147, filed on 10 Sep. 2019, and published as WO2020/125080 on 25 Jun. 2020, which claims the benefit under 35 U.S.C. 119 to Chinese Patent Application No. 201811542627.4 filed on Dec. 17, 2018 and titled "CT SYSTEM AND DETECTION APPARATUS FOR CT SYSTEM", the benefit of priority of each of which is claimed herein, and which applications and publication are hereby incorporated herein by reference in their entirety.

TECHNICAL FIELD

The present application relates to the field of radiation detection, and particularly to a CT system and a detection apparatus for the CT system.

BACKGROUND

At present, the computer tomography (CT) technology based on radiographic imaging is widely used in security check, especially for detecting suspicious items in luggage. In the CT technology based on radiographic imaging, the feature distribution data of the scanned object in the tomography can be obtained through CT data reconstruction, and common suspect substances in luggage can be identified by analyzing the feature distribution data.

The current dual-energy CT system commonly used utilizes a dual-layer detector structure to obtain dual-energy projection data to distinguish the object under inspection. However, the dual-layer detector structure in the current CT system can only provide the dual-energy projection data at most, which limits the ability to distinguish materials.

SUMMARY

Embodiments of the present application provide a CT system and a detection apparatus for the CT system.

According to one aspect of the embodiments of the present application, a detection apparatus for a CT system is provided, comprising:
  a high-energy detector assembly comprising a plurality of rows of high-energy detectors arranged along a predetermined trajectory;
  a low-energy detector assembly comprising a plurality of rows of low-energy detectors arranged at intervals along the predetermined trajectory, the low-energy detector assembly and the high-energy detector assembly being disposed in a stack;
  wherein a number of rows of the low-energy detectors is smaller than a number of rows of the high-energy detectors; and
  each row of the low-energy detectors covers a row of the high-energy detectors.

In an embodiment, any two adjacent rows of the high-energy detectors are closely arranged.

In an embodiment, the plurality of rows of the high-energy detectors are arranged at intervals along the predetermined trajectory.

In an embodiment, any two adjacent rows of the high-energy detectors are separated by a first preset interval.

In an embodiment, at least one row of the high-energy detectors not covered by the low-energy detectors is arranged between any two adjacent rows of the high-energy detectors covered by the low-energy detectors.

In an embodiment, the high-energy detectors covered by the low-energy detectors and the high-energy detectors not covered by the low-energy detectors are alternately arranged along the predetermined trajectory.

In an embodiment, any two adjacent rows of the low-energy detectors are separated by a second preset interval.

In an embodiment, the second preset interval is 5 mm to 80 mm; or
  the second preset interval is 30 mm to 50 mm.

In an embodiment, the predetermined trajectory is a circular arc.

According to another aspect of the embodiments of the present application, a detection apparatus for a CT system is provided, comprising:
  a first layer detector assembly, a second layer detector assembly, . . . , and a N-th layer detector assembly being stacked, where N is an integer greater than 2;
  wherein the first layer detector assembly comprises a plurality of rows of first detectors arranged along a predetermined trajectory, the second layer detector assembly comprises a plurality of rows of second detectors arranged at intervals along the predetermined trajectory, . . . , and the N-th layer detector assembly comprises a plurality of rows of N-th detectors arranged at intervals along the predetermined trajectory;
  an energy corresponding to an energy response peak of the first detectors, an energy corresponding to an energy response peak of the second detectors, . . . , and an energy corresponding to an energy response peak of the N-th detectors successively decrease;
  a number of rows of detectors in a (k+1)-th layer detector assembly is smaller than a number of rows of detectors in a k-th layer detector assembly, where k=1, 2, . . . , N−1; and
  each row of the detectors in the (k+1)-th layer detector assembly covers a row of the detectors in the k-th layer detector assembly.

According to yet another aspect of the embodiments of the present application, a CT system is provided, comprising:
  a scanning channel for an object under inspection to enter and exit the CT system;
  a slip ring configured to rotate around the scanning channel;
  a radiation source connected with the slip ring; and
  a detection apparatus arranged oppositely to the radiation source and connected with the slip ring, wherein the detection apparatus is the detection apparatus provided by the embodiments of the present application.

In an embodiment, the CT system further comprises a data processing module configured to reconstruct a CT image of the object under inspection based on a data signal output by the detection apparatus.

BRIEF DESCRIPTION OF THE DRAWINGS

Features, advantages, and technical effects of the exemplary embodiments of the present application will be described below with reference to the accompanying drawings.

DETAILED DESCRIPTION

Implementation of the present application will be described in further detail below in conjunction with the accompanying drawings and the embodiments. The following detailed description of the embodiments and the drawings are used to exemplarily illustrate the principle of the present application, but should not be used to limit the scope of the present application, that is, the present application is not limited to the described embodiments.

It should be noted that, in the present application, relational terms such as first and second are used merely to distinguish one entity or operation from another entity or operation, without necessarily requiring or implying any actual such relationships or orders of these entities or operations. Moreover, the terms "comprise", "include", or any other variants thereof, are intended to represent a non-exclusive inclusion, such that a process, method, article or device including a series of elements includes not only those elements, but also other elements that are not explicitly listed or elements inherent to such a process, method, article or device. Without more constraints, the elements following an expression "comprise/include . . . " do not exclude the existence of addition identical elements in the process, method, article or device that includes the elements.

For a better understanding of the present application, a CT system and a detection apparatus for the CT system according to the embodiments of the present application will be described in detail below in conjunction with the drawings. It should be noted that these embodiments are not used to limit the scope of disclosure of the present application.

Figure 1:
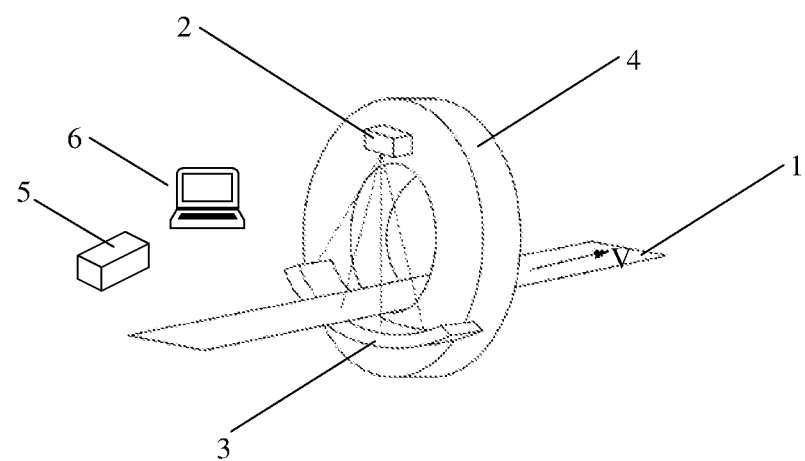
FIG. 1 shows a schematic structural diagram of a CT system provided by some embodiments of the present application.

FIG. 1 shows a schematic structural diagram of a CT system provided by the embodiments of the present application. As shown in FIG. 1, the CT system includes: a scanning channel 1, a radiation source 2, a detection apparatus 3, a slip ring 4, a control apparatus 5, and a data processing apparatus 6.

In the embodiments of the present application, an object under inspection enters and exits the CT system through the scanning channel 1 along the transfer direction V.

The radiation source 2 is connected with the slip ring and used to emit a beam of rays. The radiation source 2 may be a variety of types of commonly used X-ray machines and accelerators, and may also be an apparatus capable of emitting X-ray or γ-ray, such as radioisotopes and synchrotron radiation light sources.

The detection apparatus 3 is arranged oppositely to the radiation source 2 and connected with the slip ring 4. The detection apparatus 3 receives the beam of rays emitted by the radiation source 2 passing through the object under inspection.

The slip ring 4 rotates around the scanning channel 1. Herein, the rotation axis of the slip ring 4 is substantially parallel to the transfer direction V along which the scanning channel 1 transfers the object under inspection. The slip ring 4 rotates according to the preset scanning parameters to drive the radiation source 2 and the detection apparatus 3 to rotate around the object under inspection, thereby completing a rotating scan for the object under inspection.

The control apparatus 5 controls the radiation emission of the radiation source 2 and the collection of the data signal output by the detection apparatus 3. In addition, the control apparatus 5 is also configured to control the action of the scanning channel 1 and the slip ring 4.

The data processing apparatus 6 processes the data signal generated by the detection apparatus 3 during the scanning of the object under inspection to reconstruct the CT image of the object under inspection.

Figure 2:
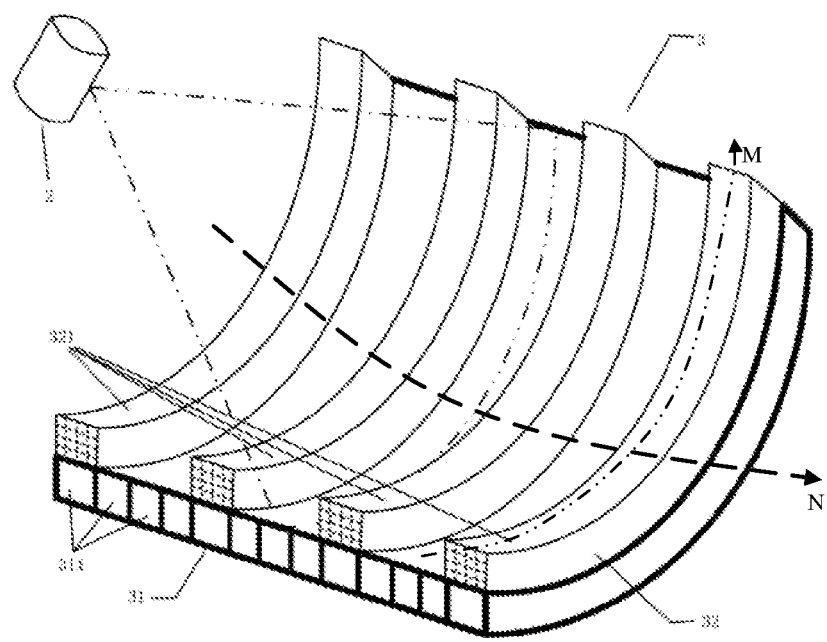
FIG. 2 shows a schematic structural diagram of a detection apparatus for a CT system provided by some embodiments of the present application.

FIG. 2 shows a schematic structural diagram of a detection apparatus 3 provided by an embodiment of the present application. Referring to FIG. 2, the detection apparatus 3 includes:

a high-energy detector assembly 31 including a plurality of rows of high-energy detectors 311 arranged along a predetermined trajectory; and a low-energy detector assembly 32 including a plurality of rows of low-energy detectors 321 arranged at intervals along the predetermined trajectory, the low-energy detector assembly 32 and the high-energy detector assembly 31 being disposed in a stack.

Herein, the low-energy detector assembly 32 is arranged at the side close to the radiation source 2, and the high-energy detector assembly 31 is arranged at the side far away from the radiation source 2. That is, the ray emitted by the radiation source 2 first enters the low-energy detector 321.

Still referring to FIG. 2, the high-energy detector assembly 31 includes an area array high-energy detector 311 arranged along the circular arc trajectory N shown by the dotted line with an arrow in FIG. 2. Herein, the area array high-energy detector includes a plurality of rows of the high-energy detectors 311, and any two adjacent rows of the high-energy detectors 311 are closely arranged. In other words, the distance between any two adjacent rows of the high-energy detectors 311 is infinitely close to zero. Optionally, the centers of the high-energy detection units of the area array may be distributed on a circular arc centered with the focal point of the radiation source 2.

Alternatively, the predetermined trajectory of the arrangement of the plurality of rows of the high-energy detectors is a straight line parallel to the transfer direction V.

Figure 3:
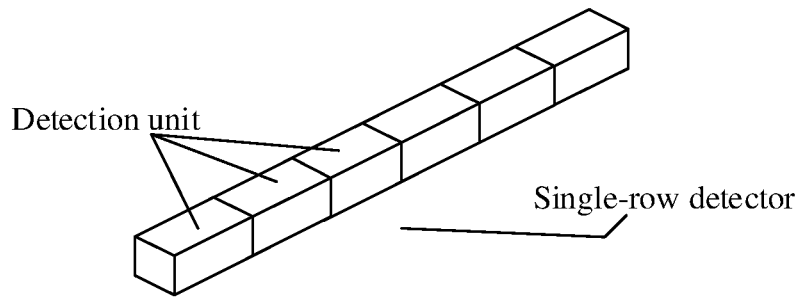
FIG. 3 shows a schematic structural diagram of a single-row detector provided by some embodiments of the present application.

FIG. 3 shows a schematic structural diagram of a single-row detector provided by the embodiments of the present application. The single-row detector here may be a single-row low-energy detector or a single-row high-energy detector. As shown in FIG. 3, the single-row detector is formed by arranging a plurality of detection units along a predetermined trajectory. Herein, each detection unit independently outputs a piece of data. Alternatively, the plurality of the detection units may be arranged continuously or at intervals.

In the embodiments of the present application, each row of the high-energy detectors includes a plurality of high-energy detection units arranged along a predetermined trajectory. Referring to FIG. 2, the plurality of the high-energy detection units are arranged along the arc trajectory M of FIG. 2. Alternatively, the plurality of the high-energy detection units in each row of the high-energy detectors may be arranged along a straight line.

In the embodiments of the present application, the arrangement trajectory of the high-energy detection units in the high-energy detector may be a straight line substantially parallel to the transfer direction V of the scanning channel. That is, the plurality of the high-energy detection units are arranged along the transfer direction of the scanning channel. The arrangement trajectory of the high-energy detection units in the high-energy detector may also be a circular arc centered with the focal point of the radiation source.

In the embodiments of the present application, the low-energy detector assembly 32 includes a plurality of rows of the low-energy detectors 321 arranged at intervals along the circular arc trajectory N of FIG. 2. Optionally, the distances between two adjacent rows of the low-energy detectors 321 may be equal or unequal.

Alternatively, the distances between every two adjacent rows of the low-energy detectors are equal. The distance between every two adjacent rows of the low-energy detectors 321 may be 5 mm to 80 mm, 10 mm to 70 mm, 20 mm to 60 mm, 30 mm to 50 mm, 35 mm to 45 mm, 36 mm to 40 mm, or 38 mm Specifically, the distance may be set according to the requirement of the object under inspection.

Herein, each row of the low-energy detectors includes a plurality of low-energy detection units arranged along a predetermined trajectory. Referring to FIG. 2, the plurality of the low-energy detection units in each row of the low-energy detectors are also arranged along the arc trajectory of FIG. 2. Alternatively, the plurality of the low-energy detection units in each row of the low-energy detectors may also be arranged along a straight line parallel to the transfer direction V.

In the embodiments of the present application, a number of rows of the low-energy detectors 321 is smaller than a number of rows of the high-energy detectors 311, and each row of the low-energy detectors 321 covers a row of the high-energy detectors 311. Since the number of rows of the low-energy detectors 321 is smaller than the number of rows of the high-energy detectors 311, the high-energy detector assembly includes high-energy detectors covered by low-energy detectors and high-energy detectors not covered by low-energy detectors.

Figure 4:
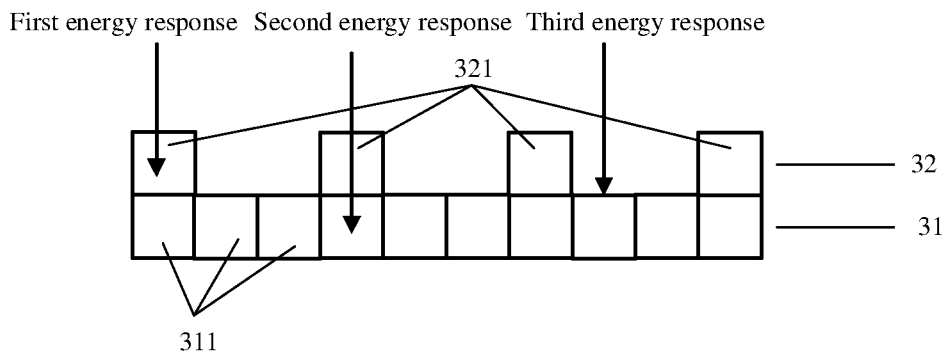
FIG. 4 shows a side view of the detection apparatus of FIG. 2.
Figure 5:
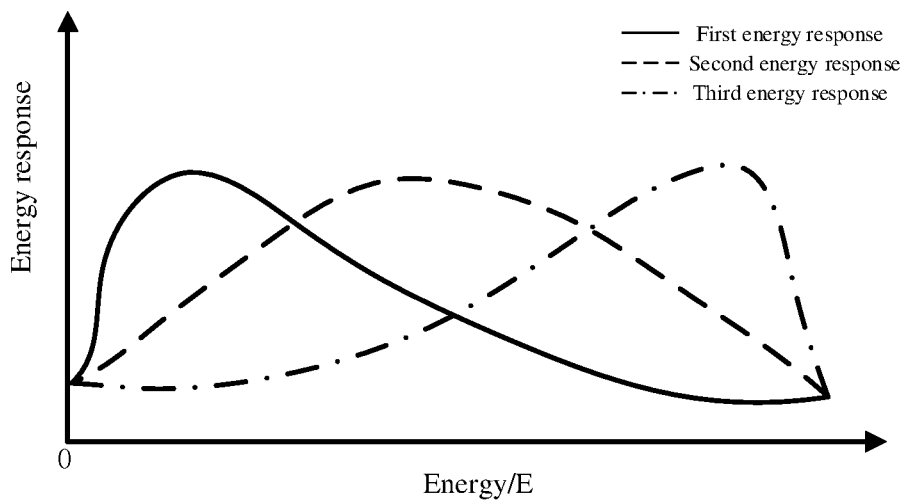
FIG. 5 shows the energy response curves of the low-energy detector and the high-energy detector in the detection apparatus of FIG. 2.

FIG. 4 shows a side view of the detection apparatus of FIG. 2. FIG. 5 shows the energy response curves of the low-energy detector and the high-energy detector of FIG. 2. As shown in FIG. 4, in the use of the CT system, with the detection apparatus of FIG. 2, the X-ray emitted by the radiation source 2 passes through the detection apparatus in three ways: the X-ray directly enters the low-energy detector 321 and deposits, the X-ray passing through the low-energy detector 321 then enters the high-energy detector covered by the low-energy detector and deposits, and the X-ray directly enters the high-energy detector not covered by the low-energy detector and deposits.

Herein, since the number of rows of the low-energy detectors 321 is smaller than the number of rows of the high-energy detectors 311, the high-energy detector assembly includes the high-energy detectors not covered by the low-energy detectors. Therefore, the X-ray can directly deposit at the high-energy detectors not covered by the low-energy detectors.

Since each row of the low-energy detectors 321 covers a row of the high-energy detectors 311, the ray passing through the low-energy detector can deposit at the high-energy detector covered by the low-energy detector.

As shown in FIG. 5, the solid line represents a first energy response curve of the low-energy detector, the dotted line represents a second energy response curve of the high-energy detector covered by the low-energy detector, and the dot-and-dash line represents a third energy response curve of the high-energy detector not covered by the low-energy detector.

Referring to FIGS. 4 and 5, after the X-ray deposits at the low-energy detector, the first energy response of the low-energy detector 321 is relatively remarkable in the low-energy range.

When the X-ray directly deposits at the high-energy detector not covered by the low-energy detector, the third energy response of the high-energy detector not covered by the low-energy detector is relatively remarkable in the high-energy range.

After the X-ray passes through the low-energy detector and deposits at the high-energy detector covered by the low-energy detector, the high-energy detector covered by the low-energy detector has a second energy response that is different from the first energy response, and the second energy response is a multiplication of the first energy response and the third energy response. Referring to FIG. 5, the second energy response is relatively remarkable in the intermediate-energy range between the low-energy range and the high-energy range.

Still referring to FIG. 5, for the three types of detectors, i.e., the low-energy detector, the high-energy detector covered by the low-energy detector, and the high-energy detector not covered by the low-energy detector, the energy of the photon with the largest deposition proportion in each of the three types of detectors are different.

That is, the energy corresponding to the peak of the first energy response of the low-energy detector, the energy corresponding to the peak of the second energy response of the high-energy detector covered by the low-energy detector, and the energy corresponding to the peak of the third energy response of the high-energy detector not covered by the low-energy detector successively increase.

Therefore, the CT system using the detection apparatus provided by the embodiments of the present application can obtain a tri-energy projection data of the object under inspection. Compared with a dual-energy projection image, the tri-energy projection image can more accurately describe the attenuation coefficient function of the scanned material, and thus has a stronger ability to distinguish materials.

In the embodiments of the present application, no other devices are arranged between the low-energy detector assembly and the high-energy detector assembly, such that the ray emitted by the radiation source can directly deposit at the high-energy detector not covered by the low-energy detector, and also deposit at the high-energy detector covered by the low-energy detector, thereby obtaining the tri-energy projection data utilizing two layers of detector assemblies to improve the ability to distinguish materials.

As an example, for two different materials A and B, the attenuation coefficient function of the material A has a K-edge jump, and the attenuation coefficient function of the material B does not have a K-edge jump but is generally similar to the attenuation coefficient function of the material A. Herein, K-edge is the binding energy of electron in the K-layer of an atom. If the energy of a photon exceeds the K-edge, the interaction between the electron in the K-layer of the atom and the photon will produce the photoelectric effect, and the attenuation coefficient function of the atom will jump.

Since the X-ray energy spectrum has an obvious energy broadening, the attenuation coefficient of the material A reconstructed from the dual-energy projection data is an average of the attenuation coefficient function of the material A on the X-ray energy spectrum, i.e., an equivalent attenuation coefficient, which is very close to the reconstructed equivalent attenuation coefficient of the material B, that is, the material A and the material B are not distinguishable from the dual-energy projection data.

The detection apparatus provided by the embodiments of the present application can provide the tri-energy projection data, which can provide the equivalent attenuation coefficient under three different energy spectra. Compared with the dual-energy equivalent attenuation coefficient, the additional one dimension of data is used to reflect whether there is a K-edge jump, thus the material A and the material B are distinguishable, and the ability to distinguish materials is improved.

In the embodiments of the present application, the low-energy detector assembly 32 is arranged at the side close to the radiation source 2, not the high-energy detector assembly 31 is arranged at the side close to the radiation source 2, such that the ray emitted by the radiation source can pass through the low-energy detector assembly and then enter the high-energy detector covered by the low-energy detector, and in turn the projection data with the second energy response is obtained.

If the high-energy detector assembly 31 is arranged at the side close to the radiation source 2 and the low-energy detector assembly 32 is arranged at the side far away from the radiation source 2, the tri-energy projection data cannot be obtained. Generally, the thickness of the high-energy detector is relatively large, and thus all the photons in the ray will deposit in the high-energy detector. If the high-energy detector assembly 31 is arranged at the side close to the radiation source 2, no photons are incident in the low-energy detector covered by the high-energy detector, and thus only the dual-energy projection data can be obtained.

The detection crystal in the high-energy detector is generally thick. Therefore, the high-energy detector assembly arranged at the side far away from the radiation source 2 can completely absorb the photons of the X-ray emitted by the radiation source, and thus the detection apparatus in the embodiments of the present application has high detection efficiency, less image noise, and strong penetrability.

In the embodiments of the present application, the high-energy detector covered by the low-energy detector has the second energy response, and the high-energy detector not covered by the low-energy detector has the third energy response. To further improve the image quality of the object under inspection, and to improve the uniformity and accuracy of the projection data with the third energy response in the high-energy detector assembly, the high-energy detection units in the high-energy detector assembly may be standardized or calibrated.

As an example, the first data respectively output by the plurality of the high-energy detection units in the high-energy detector when it is not covered by the low-energy detector is first obtained; then the high-energy detector is covered by the low-energy detector to obtain the second data respectively output by the plurality of the high-energy detection units in the high-energy detector when it is covered by the low-energy detector, and the third data respectively output by the plurality of the low-energy detection units in the low-energy detector. Then, the relationship between the first data and the second data, the third data is established according to a plurality of the first data, a plurality of the second data, and a plurality of the third data.

As a specific example, the relationship between the first data and the second data, the third data is established by taking the first data as the independent variable and the second data and the third data as the dependent variables, thereby calculating, if a weighted sum of the second data and the third data is used to estimate the first data, the weight corresponding to the second data and the weight corresponding to the third data.

For each high-energy detection unit in the high-energy detector covered by the low-energy detector in the detection apparatus, according to the pre-standardized weights of the second data and the third data, the third data of the low-energy detection unit covering the high-energy detection unit and the second data of this high-energy detection unit are weighted and summed to estimate, for each high-energy detection unit in the high-energy detector covered by the low-energy detector, the estimated projection data when it is not covered by the low-energy detector.

Then, the estimated projection data corresponding to each high-energy detection unit in the high-energy detector covered by the low-energy detector are combined with the projection data output by the high-energy detection unit in other high-energy detector not covered by the low-energy detector to construct the projection data of the high-energy detector with only the third energy response, thereby providing a single-energy three-dimensional reconstruction result of the object under inspection.

Through improving the consistency of the data output by the high-energy detectors in the high-energy detector assembly, more data of the object under inspection can be obtained, the data uniformity and the image quality are improved, and thus the ability to distinguish materials is further improved.

Figure 6:
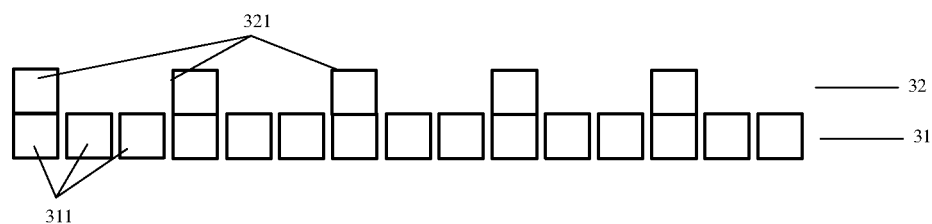
FIG. 6 shows a side view of a detection apparatus provided by another embodiment of the present application.

FIG. 6 shows a side view of a detection apparatus provided by another embodiment of the present application. The detection apparatus shown in FIG. 6 differs from the detection apparatus shown in FIG. 2 in that:

the plurality of rows of the high-energy detectors in the high-energy detector assembly are arranged at intervals along the predetermined trajectory.

Herein, the distances between any two adjacent rows of the high-energy detectors may be equal or unequal. Alternatively, the distances between any two adjacent rows of the high-energy detectors may be equal to maintain the spatial uniformity and image quality of the data output by the high-energy detectors.

In the embodiments of the present application, if the distances between every two adjacent rows of the low-energy detectors are equal, and the distances between every two adjacent rows of the high-energy detectors are also equal, the row distance of the low-energy detectors is greater than the row distance of the high-energy detectors to ensure that the high-energy detector assembly includes the high-energy detectors not covered by the low-energy detectors.

In the embodiments of the present application, at least one row of the high-energy detectors not covered by the low-energy detectors is arranged between any two adjacent rows of the high-energy detectors covered by the low-energy detectors to maintain the data uniformity and image quality.

Specifically, the high-energy detectors covered by the low-energy detectors and the high-energy detectors not covered by the low-energy detectors are alternately arranged along the predetermined trajectory to ensure a uniform distribution of the projection data with the second energy response and the projection data with the third energy response, thereby improving the image quality of the object under inspection to further improve the ability to distinguish materials.

The embodiments of the present application further provide a detection apparatus including:
a first layer detector assembly, a second layer detector assembly, ..., and a N-th layer detector assembly being stacked, where N is an integer greater than 2;
herein the first layer detector assembly includes a plurality of rows of first detectors arranged along a predetermined trajectory, the second layer detector assembly includes a plurality of rows of second detectors arranged at intervals along the predetermined trajectory, ..., and the N-th layer detector assembly includes a plurality of rows of N-th detectors arranged at intervals along the predetermined trajectory;
an energy corresponding to an energy response peak of the first detectors, an energy corresponding to an energy response peak of the second detectors, ..., and an energy corresponding to an energy response peak of the N-th detectors successively decrease;
a number of rows of detectors in a (k+1)-th layer detector assembly is smaller than a number of rows of detectors in a k-th layer detector assembly, where k=1, 2, ..., N−1; and
each row of the detectors in the (k+1)-th layer detector assembly covers a row of the detectors in the k-th layer detector assembly.

Figure 7:
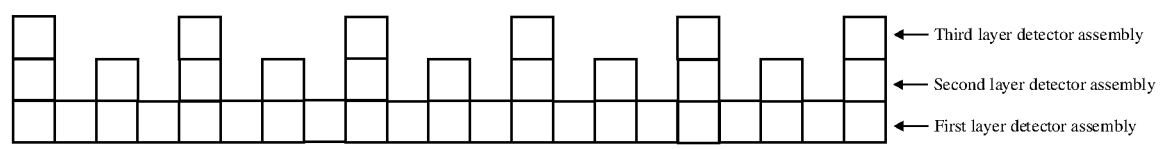
FIG. 7 shows a side view of a detection apparatus provided by yet another embodiment of the present application.

As an example, FIG. 7 shows a side view of the detection apparatus when N=3. By providing a plurality of layers of detector assemblies, the multi-energy projection data such as quadr-energy and more-energy projection data of the object under inspection can be obtained, thereby further improving the ability to distinguish materials.

Detection apparatuses including three or more layers of detector assemblies provided according to the embodiments of the present application are similar to the detection apparatuses of FIG. 2 to FIG. 6 including two layers of detector assemblies, and will not be repeated here.

Although the present application has been described with reference to the preferred embodiments, various modifications can be made and the components therein can be replaced with equivalents without departing from the scope of the present application. In particular, as long as there is no structural conflict, the various technical features mentioned in the various embodiments can be combined in any manner. The present application is not limited to the specific embodiments disclosed herein, and includes all technical solutions falling within the scope of the claims.

What is claimed is:

1. A detection apparatus for a CT system, comprising:
a high-energy detector assembly comprising a plurality of rows of high-energy detectors arranged along a predetermined trajectory; and
a low-energy detector assembly comprising a plurality of rows of low-energy detectors arranged at intervals along the predetermined trajectory, the low-energy detector assembly and the high-energy detector assembly being disposed in a stack;
wherein a number of rows of the low-energy detectors is smaller than a number of rows of the high-energy detectors; and
each row of the low-energy detectors covers a row of the high-energy detectors.

2. The detection apparatus of claim 1, wherein any two adjacent rows of the high-energy detectors are closely arranged.

3. The detection apparatus of claim 1, wherein the plurality of rows of the high-energy detectors are arranged at intervals along the predetermined trajectory.

4. The detection apparatus of claim 1, wherein any two adjacent rows of the high-energy detectors are separated by a first preset interval.

5. The detection apparatus of claim 1, wherein at least one row of the high-energy detectors not covered by the low-energy detectors is arranged between any two adjacent rows of the high-energy detectors covered by the low-energy detectors.

6. The detection apparatus of claim 1, wherein the high-energy detectors covered by the low-energy detectors and the high-energy detectors not covered by the low-energy detectors are alternately arranged along the predetermined trajectory.

7. The detection apparatus of claim 1, wherein any two adjacent rows of the low-energy detectors are separated by a second preset interval.

8. The detection apparatus of claim 7, wherein the second preset interval is 5 mm to 80 mm; or the second preset interval is 30 mm to 50 mm.

9. The detection apparatus of claim 1, wherein the predetermined trajectory is a circular arc.

10. A CT system, comprising:
a scanning channel for an object under inspection to enter and exit the CT system;
a slip ring configured to rotate around the scanning channel;
a radiation source connected with the slip ring; and
a detection apparatus arranged oppositely to the radiation source and connected with the slip ring, wherein the detection apparatus is the detection apparatus of claim 1.

11. The CT system of claim 10, further comprising:
a data processing module configured to reconstruct a CT image of the object under inspection based on a data signal output by the detection apparatus.

12. A detection apparatus for a CT system, comprising:
a first layer detector assembly, a second layer detector assembly, ..., and a N-th layer detector assembly being stacked, where N is an integer greater than 2;
wherein the first layer detector assembly comprises a plurality of rows of first detectors arranged along a predetermined trajectory, the second layer detector assembly comprises a plurality of rows of second detectors arranged at intervals along the predetermined trajectory, ..., and the N-th layer detector assembly comprises a plurality of rows of N-th detectors arranged at intervals along the predetermined trajectory;
an energy corresponding to an energy response peak of the first detectors, an energy corresponding to an energy response peak of the second detectors, ..., and an energy corresponding to an energy response peak of the N-th detectors successively decrease;
a number of rows of detectors in a (k+1)-th layer detector assembly is smaller than a number of rows of detectors in a k-th layer detector assembly, where k=1, 2, ..., N−1; and
each row of the detectors in the (k+1)-th layer detector assembly covers a row of the detectors in the k-th layer detector assembly.

* * * * *